United States Patent
Beerwerth et al.

(10) Patent No.: US 10,543,040 B2
(45) Date of Patent: *Jan. 28, 2020

(54) SKIN TREATMENT DEVICE

(71) Applicant: Braun GmbH, Kronberg (DE)

(72) Inventors: Frank Beerwerth, Kaltenholzhausen (DE); Christian Neyer, Eschborn (DE); Dalibor Dadic, Koenigstein (DE); Felix Heinemann, Frankfurt am Main (DE)

(73) Assignee: Braun GMBH, Kronberg (DE)

(*) Notice: Subject to any disclaimer, the term of this patent is extended or adjusted under 35 U.S.C. 154(b) by 39 days.

This patent is subject to a terminal disclaimer.

(21) Appl. No.: 15/419,229

(22) Filed: Jan. 30, 2017

(65) Prior Publication Data

US 2017/0215959 A1  Aug. 3, 2017

(30) Foreign Application Priority Data

Feb. 2, 2016 (EP) .................................... 16153813
Jan. 19, 2017 (EP) .................................... 17152188

(51) Int. Cl.
*A61B 18/18* (2006.01)
*H01L 25/075* (2006.01)
(Continued)

(52) U.S. Cl.
CPC .............. *A61B 18/18* (2013.01); *A45D 26/00* (2013.01); *A61B 18/1815* (2013.01);
(Continued)

(58) Field of Classification Search
CPC . A61B 18/18; A61B 2018/1807; A61B 18/20; A61B 18/203; A61B 2018/00315;
(Continued)

(56) References Cited

U.S. PATENT DOCUMENTS 6,645,230 B2 * 11/2003 Whitehurst .......... A61N 5/0613
                                                                      607/88
6,663,659 B2    12/2003 McDaniel
(Continued)

FOREIGN PATENT DOCUMENTS

JP    2007044091    2/2007
WO    WO-2006/005443    1/2006

OTHER PUBLICATIONS

U.S. Appl. No. 15/419,214, filed Jan. 30, 2017, Frank Beerwerth et al.

(Continued)

*Primary Examiner* — Ahmed M Farah
(74) *Attorney, Agent, or Firm* — Kevin C. Johnson (57) ABSTRACT

The present invention is concerned with a skin treatment device, in particular a hair removal device, having a light emission unit comprising a substrate and a plurality of first LED dies mounted on the substrate on an area of at least 0.2 cm$^2$, in particular of at least 1 cm$^2$, wherein the skin treatment device is arranged to activate the first LED dies to emit a treatment light pulse having a pulse length in particular in the range of between 10 ms and 300 ms and the first LED dies have a radiant flux such that a radiant fluence on the skin of a user of at least 1 J/cm$^2$ is achieved by application of the treatment light pulse, wherein the light emission unit has at least two selectable active areas of first LED dies, where the selectable active areas have different sizes, and at least three second LED dies are mounted on the substrate at locations suitable for visibly indicating each of the selectable active areas.

19 Claims, 6 Drawing Sheets

(51) Int. Cl.
*H01L 33/48* (2010.01)
*H01L 33/60* (2010.01)
*H01L 33/62* (2010.01)
*H01L 33/64* (2010.01)
*A45D 26/00* (2006.01)
*A61B 18/00* (2006.01)
*H01L 31/147* (2006.01)

(52) U.S. Cl.
CPC ........ *H01L 25/0753* (2013.01); *H01L 33/486* (2013.01); *H01L 33/60* (2013.01); *H01L 33/62* (2013.01); *H01L 33/642* (2013.01); *A61B 2018/00476* (2013.01); *A61B 2018/1807* (2013.01); *H01L 31/147* (2013.01)

(58) Field of Classification Search
CPC .. A61B 2018/00452; A61B 2018/0047; A61B 2018/00476; A61N 5/06; A61N 5/0613; A61N 5/0616; A61N 5/0617; A61N 2005/0652; A61N 2005/0658; A61N 2005/0659; A61N 2005/0661; A61N 2005/0662
USPC ................................ 606/3, 9–11; 607/88–92
See application file for complete search history.

(56) References Cited

U.S. PATENT DOCUMENTS

| | | |
|---|---|---|
| 8,961,578 B2 | 2/2015 | Liu et al. |
| 9,375,281 B2 | 6/2016 | Moench et al. |
| 2004/0191729 A1* | 9/2004 | Altshuler ........... A46B 15/0002 433/215 |
| 2005/0231983 A1* | 10/2005 | Dahm ................. A61C 19/003 362/294 |
| 2006/0206173 A1* | 9/2006 | Gertner ................ A61N 5/0616 607/88 |
| 2007/0038206 A1* | 2/2007 | Altshuler ............ A61B 18/203 606/20 |
| 2007/0185553 A1 | 8/2007 | Kennedy |
| 2007/0198004 A1 | 8/2007 | Altshuler et al. |
| 2007/0208395 A1* | 9/2007 | Leclerc ................ A61N 5/0616 607/86 |
| 2007/0255355 A1* | 11/2007 | Altshuler ............. A61B 18/203 607/86 |
| 2008/0060148 A1* | 3/2008 | Pinyayev ............ A61B 5/0088 15/22.1 |
| 2009/0018621 A1 | 1/2009 | Vogler et al. |
| 2010/0114007 A1 | 5/2010 | Fischer et al. |
| 2010/0145321 A1 | 6/2010 | Altshuler et al. |
| 2011/0238138 A1 | 9/2011 | Takada |
| 2012/0116373 A1 | 5/2012 | Moench et al. |
| 2012/0226268 A1* | 9/2012 | Liu ...................... A61B 18/203 606/9 |
| 2012/0295376 A1* | 11/2012 | Lee ...................... A61N 5/0622 438/28 |
| 2014/0114231 A1* | 4/2014 | Rostro .................. A61N 5/062 604/20 |
| 2014/0303547 A1 | 10/2014 | Loupis et al. |
| 2016/0256706 A1* | 9/2016 | Harrison .............. A61N 5/0622 |
| 2016/0263395 A1* | 9/2016 | Siegel .................. A61B 5/4836 |
| 2017/0215958 A1* | 8/2017 | Beerwerth ............ A61B 18/18 |
| 2017/0216619 A1* | 8/2017 | Beerwerth ........... A61N 5/0616 |

OTHER PUBLICATIONS

U.S. Appl. No. 15/419,245, filed Jan. 30, 2017, Frank Beerwerth et al.
U.S. Appl. No. 15/419,254, filed Jan. 30, 2017, Frank Beerwerth et al.

* cited by examiner

SKIN TREATMENT DEVICE

FIELD OF THE INVENTION

The present invention is concerned with a skin treatment device, in particular with a temporal hair removal device, comprising a plurality of LED dies.

BACKGROUND OF THE INVENTION

It is known that skin can be treated with relatively high intensity light in order to achieve certain effects such as skin rejuvenation and in particular (temporal) hair removal (a.k.a. temporal hair growth reduction). Most known light based skin treatment devices suitable for at least temporal hair removal make use of laser light sources or flash lamps as both light sources can provide high intensity light in short pulses. LEDs have generally been described as one alternative light source for skin treatment.

Document US 2012/0116373 A1 discloses a light application apparatus for applying light to an object. The apparatus comprises a light source for generating processing light and sensing light, where a control unit controls the light source such that processing light in a processing time interval and sensing light in a sensing time interval are generated alternately. The light source is preferentially a solid state light source, in particular a light emitting diode or a laser diode. It is preferred that the light source comprises a VCSEL. The processing light preferentially has a wavelength in the range of 570-1200 nm and an energy density in the range of 2-30 J/cm$^2$ and a pulse duration within 1 to 600 ms.

It is an object of the present disclosure to provide a skin treatment device comprising a plurality of LED dies that is improved over the known devices or at least provides an alternative.

SUMMARY OF THE INVENTION

In accordance with one aspect there is provided a skin treatment device, in particular a hair removal device, having a light emission unit comprising a substrate and a plurality of first LED dies mounted on the substrate on an area of at least 0.2 cm$^2$, in particular of at least 1 cm$^2$, wherein the skin treatment device is arranged to activate the first LED dies to emit a treatment light pulse having a pulse length in particular in the range of between 10 ms and 300 ms and the first LED dies have a radiant flux such that a radiant fluence on the skin of a user of at least 1 J/cm$^2$ is achieved by application of the treatment light pulse, wherein the light emission unit has at least two selectable active areas of first LED dies, where the selectable active areas have different sizes, and at least three second LED dies are mounted on the substrate at locations suitable for visibly indicating each of the selectable active areas.

In accordance with one aspect there is provided a method of cosmetic skin treatment, in particular of cosmetic hair removal, comprising the steps of:
  providing a substrate;
  mounting a plurality of first LED dies onto the substrate on an area of at least 0.2 cm$^2$, in particular of at least 1 cm$^2$, which first LED dies are arranged for emitting light with a peak emission wavelength in the wavelength range of between 480 nm and 980 nm;
  mounting at least three second LEDs onto the substrate at locations suitable for visibly indicating each one of at least two selectable active areas of the plurality of first LEDs;
  selecting an active area from the at least two selectable active areas;
  activating the first LED dies assigned to the selected active area to emit a treatment light pulse; and
  activating at least two of the at least three second LEDs to emit visible light to indicate the selected active area outside of the duration of the treatment light pulse.

BRIEF DESCRIPTION OF THE DRAWINGS

The present disclosure will be further elucidated by a description of example embodiments in which description reference is made to figures. In the figures

DETAILED DESCRIPTION OF THE INVENTION

It is generally known that various types of skin treatment can be affected by applying light (in particular in the form of at least one treatment light pulse) to the skin. Such skin treatments encompass skin rejuvenation, wrinkle reduction, acne treatment, and (temporal and permanent) hair removal (also named hair growth reduction or hair growth management, as hairs are not necessarily immediately removed by the application of light). The skin treatments can also be grouped into cosmetic treatments such as hair removal for mere cosmetic reasons and non-cosmetic (e.g. prophylactic therapeutic) treatments. In particular, skin treatment for achieving temporal and/or permanent hair removal (hair growth reduction—in the following just "hair removal" is used) requires a radiant flux emitted by the LED die array per unit area that is much higher than the radiant flux that is required for skin rejuvenation or the like. For the application of treatment light pulses onto the skin various light sources have been discussed such as laser light sources, flash lamps (e.g. Xenon arc lamps), and semiconductor light sources such as LEDs.

While laser light sources and flash lamps have been widely discussed with respect to hair removal, the application of LEDs as light source has been discussed in much less detail, in particular as the required radiant fluence to be applied on the skin within a short pulse length (e.g. below 10 ms) are easily delivered by lasers or flash lamps. Now, the present disclosure is directed to semiconductor light sources (where in the following the term LED is used, this shall encompass other solid state light sources such as VCSELs, VECSELs, or OLEDs), in particular arrays of LED dies (i.e. semiconductor dies in contrast to packaged LEDs), and their use for light-based temporal or permanent hair removal.

LED dies can emit light at essentially any wavelength from ultraviolet (UV) light to infrared (IR) light, i.e. from about 280 nm to 1300 nm, e.g. depending on the used semiconductor material. LED dies emit light with a relatively narrow spectral bandwidth of $\Delta\lambda \cong \pm \lambda/20$. Where in the present disclosure the term "wavelength" is used in relation to an LED die, this wavelength means the peak emission wavelength, i.e. the wavelength at the maximum of the light emission curve of the LED die.

In accordance with some embodiments, the plurality of first LED dies emits light at a peak emission wavelength in the range of between 480 nm and 980 nm, in particular in the range of between 630 nm and 900 nm, and further in particular in a range of between 700 nm and 880 nm. In some embodiments, the plurality of first LED dies emit light at a peak emission wavelength in the range of between 700 nm and 760 nm or in the range of between 820 nm and 880 nm. In some embodiments, a first sub-plurality of first LED dies emit light at a peak emission wavelength in the range of between 700 nm and 760 nm (e.g. at 730 nm) and a second sub-plurality of first LED dies emit light at a peak emission wavelength in the range of between 820 nm and 880 nm (e.g. at 850 nm). In some embodiments, an additional plurality of third LED dies emits light at a peak emission wavelength in the range of between 480 nm and 510 nm. The second LED dies are arranged to emit light at a peak emission wavelength in the visible wavelength range, i.e. in the range of between 400 nm and 700 nm.

In accordance with the present description, the first LED dies are mounted on a substrate area having a certain size and the skin treatment device is arranged so that at least two different active areas can be selected for the emission of a treatment light pulse. E.g., the first LED dies are mounted on an area of 3.0 cm$^2$ and the first selectable active area may comprise the full mounted area of 3 cm$^2$ (e.g. a 3 cm times 1 cm area), while the second selectable active area is than smaller and may have an area of 1 cm$^2$ (e.g. a 1 cm times 1 cm area). This allows the user to choose between a large active area for fast treatment of large skin areas (e.g. the legs) and a small active area for slower, but more precise treatment of smaller skin areas such as the face. The smaller selectable active area may in particular have a size in the range of between 0.10 cm$^2$ to 2.0 cm$^2$, in particular in the range of between 0.36 cm$^2$ to 1.0 cm$^2$, and further in particular of around 0.64 mm$^2$.

In accordance with the present description, at least three second LED dies are mounted on the substrate at locations that are suitable for visibly indicating the selected active area, in particular when the user has made a selection. The second LED dies are then activated to emit visible light so that the size of the selected area is communicated to the user. The second LED dies are in particular located at corner or end points of the selected active areas or they may be located in close proximity to such corner or end points. As the second LED dies emit visible light outside of the duration of the treatment light pulse, the user can on the one hand identify the size of the chosen active area and can get a feeling of the location of the active area so that the user can then precisely locate the skin treatment device on the skin. While two second LED dies are considered to be sufficient to indicate the selected active area, a two-dimensional active area may also be indicated by four second LED dies located at the corners of the respective selectable active area. Further, the second LED dies may be arranged to form rings around the selectable active areas. It is implicit that a sub-plurality of first LED dies is assigned to the smaller selectable active area. A sub-plurality of second LEDs is then assigned to the smaller selectable active area for visible indication. Either all first LED dies may then be assigned to the larger selectable active area or another sub-plurality of first LED dies are assigned to the larger selectable active area, while another sub-plurality of second LED dies is assigned to the larger selectable active area. At least one second LED die may be assigned to visibly indicate two selectable active areas (e.g. because the respective indicated edge is common to both selectable areas. In some embodiments, the skin treatment device has more than two selectable active areas, e.g. three or four or five etc.

In some embodiments, the first LED dies may be arranged to emit treatment light in the far red to infrared wavelength range of between 700 nm to 980 nm, which light is essentially invisible to the human eye. Then the second LED dies can be activated to emit a visible light pulse simultaneously with the treatment light pulse. This helps the user to understand when an essentially invisible treatment light pulse was triggered. The visible light pulse does not need to have a particular energy density when it solely serves to indicate the emission of the invisible treatment light. The second LED dies may then have a radiant flux of about 100 mW or lower.

But this shall not exclude that the second LED dies can also be arranged to emit at a visible wavelength and at a radiant fluence that serves to provide an additional treatment effect.

In some embodiments, the skin treatment device can be switched between a hair removal function and another skin treatment function such as a skin rejuvenation function or an acne treatment function or a wrinkle reduction function.

In some embodiments, the skin treatment device has a control unit that is connected with the plurality of first and second LED dies for selectively activating the LED dies. The control unit may activate the first LED dies to emit a treatment light pulse, while the second LED dies are not simultaneously activated. The control unit may activate at least some of the second LED dies depending on the selected active area in a time period outside of the duration of the treatment light pulse. The control unit may also be arranged for (a) selectively switching on or off individual first LED dies during the treatment light pulse or at least during a portion of the treatment pulse or (b) controlling the forward current of at least one first LED die during the treatment light pulse.

In one aspect, the following description focuses on skin treatment devices having a light emission unit with a plurality of substrate mounted LED dies (which may be mounted in the form of a regular array pattern, but the LED dies may also be mounted in an irregular manner) that are able to deliver a radiant fluence in a range of between 1 J/cm$^2$ to 8 J/cm$^2$ (in particular of 1 J/cm$^2$ to 7 J/cm$^2$) by applying treatment light pulses in a range of between 10 ms and 300 ms, in particular in a range of between 20 ms and 200 ms, and further in particular of a range of between 30 ms and 200 ms or 30 ms and 100 ms. In the present disclosure, use is made of relatively long treatment light pulses. It is known that the coagulation needed for bringing a hair follicle into apoptosis (programmed cell death) is a function of both, temperature and time. Hence, while a temperature exposure of 70 degrees Celsius over 1 ms leads to coagulation of proteins in a hair follicle, a temperature of 62 degrees Celsius leads as well to the needed coagulation if the hair follicle is exposed to this temperature over a period of 100 ms. While a pulse length of 10 ms and higher is considered to deliver a radiant fluence in the range of 3 J/cm$^2$ and higher, which is in particular used to treat brown hair on pale skin, requires that treatment light pulses having a pulse length of at least 60 ms, further in particular of at least 100 ms are used in at least one or several treatment modes. This is in particular the case when different LED dies arranged for emitting at different wavelengths are mounted on the substrate. Thus, in accordance with at least one aspect, the skin treatment device is arranged to emit at least one treatment light pulse having a pulse length of at least 60 ms, in particular pulse lengths in a range of between 80 ms and 120 ms, typically around 100 ms.

At least some of the first LED dies mounted on the substrate have a mounting density and light output power (radiant flux) that is sufficient to affect at least temporal hair removal. This will be explained more in detail in following paragraphs.

In one aspect, the following description focuses on skin treatment devices that comprise a light emission unit with substrate mounted first LED dies comprising a first sub-plurality of first LED dies arranged for emitting at a first wavelength and at least one second sub-plurality of first LED die arranged for emitting at a second wavelength different to the first wavelength. In some embodiments, the first LED dies have a mounting density and light output power (radiant flux) sufficient for affecting at least temporal hair removal. The second LED dies may be arranged to emit visible light at a lower radiant flux sufficient for illumination purposes (e.g. the first LED dies may emit at a not visible light wavelength above about 700 nm and the second LED dies emitting visible light may then just be used for visually indicating that a treatment light pulse is being emitted). As different LED dies can easily be mounted on the same substrate, the first LED dies arranged for treatment and the second LED dies arranged for indication or illumination can be arranged on the same mounting area and can be separately controlled by respective individual wiring. In some embodiments, LED dies of the same kind are controlled as a group instead of being individually controlled. In particular, LED dies can be arranged in series and can then be controlled as a group. LED dies of a single row or column of an array of LED dies may thus be connected in series, but of course the position of the LED dies that should be controlled at the same time is arbitrary.

For sake of completeness, where the present disclosure uses the term "pulse length", this time period means the pulse length measured at full-width-half-maximum (FWHM) pulse intensity.

While the "radiant fluence" is here provided as a value on the skin of the user, it is to be understood that the skin treatment device as described herein either has the LED dies located essentially at the level of an exit opening or the substrate area mounted with LED dies is surrounded by a casing having reflective inner walls, so that the radiant fluence received by the skin of the user (during regular operation) means the radiant fluence that is emitted at the location of the LED dies because the substrate area to which the LED dies are mounted is substantially the same as the area of skin treated. In cases, where the light emitted by the LED dies is applied on the skin with a diverging beam that is not spatially limited by a reflective casing, the respective reduction factor needs to be taken into account (i.e. the radiant fluence at the LED dies level must be respectively higher than the herein defined radiant fluence on the skin).

In contrast to a flash lamp, an LED die emits in a relatively narrow wavelength band (e.g. with a spectral bandwidth (FWHM) of $\Delta\lambda \cong \pm\lambda/20$). Thus, similarly to a laser, LED dies can be chosen such that the light emitted is optimal for the particular situation (e.g. determined by hair color and/or skin color). Hence, there is than no need for optical filters that are typically used in IPL (Intense Pulsed Light) devices using a flash lamp, where the flash lamp emits in a very broad wavelength spectrum including UV portions that are to be filtered out for known health reasons.

In one aspect of the present disclosure, a skin treatment device comprises different LED dies arranged for emitting treatment light at different wavelengths, e.g. at two different wavelengths, three different wavelength etc. The second LED dies arranged for emitting light at a visible wavelength can be used to visually indicate to the user the on/off state of the device. Said device may emit a treatment light pulse in the invisible light wavelength range (e.g. in the far red or infrared (IR) light regime) and simultaneously a visible light pulse. On the other hand, first LED dies emitting light at different wavelengths can be used to optimally tune the wavelength for a particular situation (e.g. changing hair color and/or skin color from user to user or even for a single user, where in particular skin color depends on the tanning of the treatment area). These possibilities will be explained in more detail below.

Figure 1:
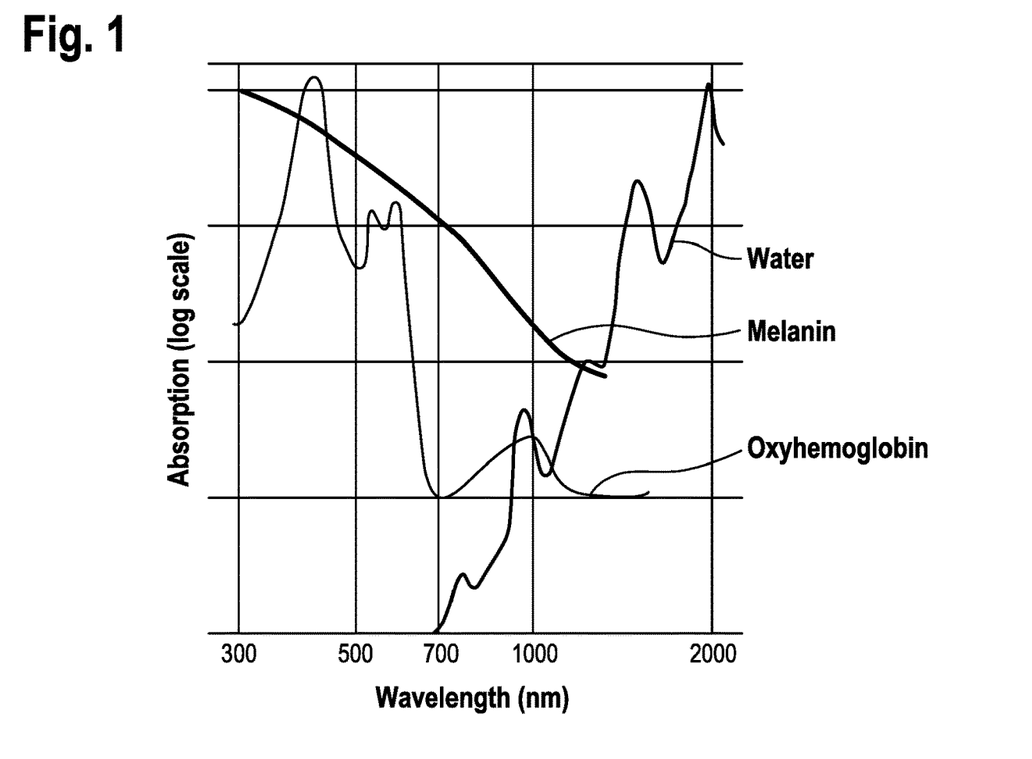
FIG. 1 is a graph showing the absorption coefficient for melanin, water, and oxyhemoglobin on a logarithmic scale vs. the wavelength of light between 300 nm and 2000 nm.

In essence, light based hair removal aims to reduce or inhibit hair growth by thermally affecting the hair follicle without affecting the surrounding skin. In order to thermally affect the hair follicle, light must be absorbed by a target chromophore in the hair follicle. Generally, the target chromophore is melanin (i.e. typically the brownish/blackish eumelanin, but also the reddish pheomelanin, which is mostly present in red hair). FIG. 1 shows the relative light absorption of melanin, oxyhemoglobin (blood), and water on a logarithmic scale in a range of between 300 nm and 2000 nm (the absorption curves of FIG. 1 are taken from: Christine C. Dierickx, M.D. "*Laser Hair Removal: Scientific Principle and Practical Aspects*", Lumenis, 2002—www.lumenis.com). Heat generated in the melanin carrying portions of the hair follicle dissipates into the surrounding tissue and eventually leads to coagulation of proteins if the heating time and the temperature together are above a certain threshold, where—as had been explained—the temperature leading to coagulation is lower if the heating time is longer.

Figure 2:
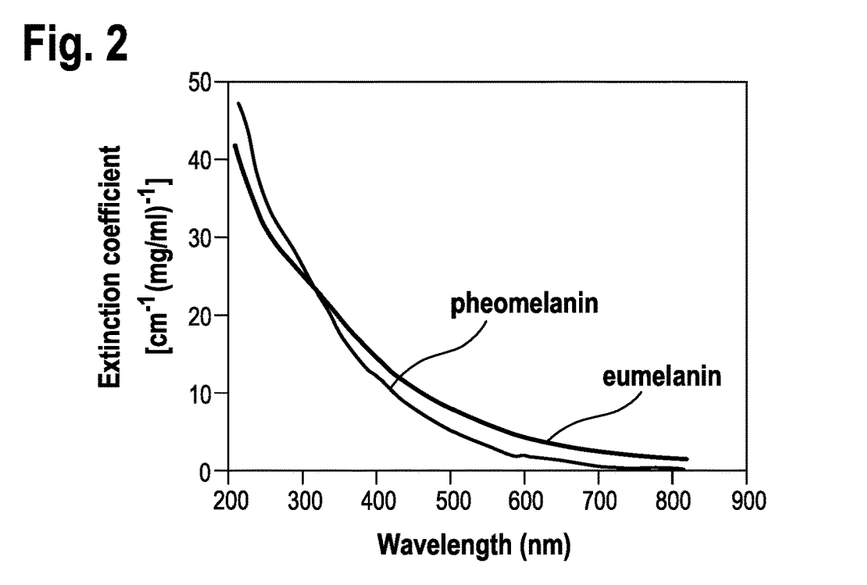
FIG. 2 is a graph showing the extinction coefficient of eumelanin and pheomelanin vs. the wavelength of light between 200 nm and 900 nm.

The present disclosure is essentially directed to a large area skin treatment device (e.g. a treatment area of at least 0.2 cm$^2$, in particular of around 1 to 4 cm$^2$, and potentially up to about 10 cm$^2$ and to unmonitored home use (i.e. allowing a user to perform the treatment at home without the risk of injuring and without the need of professional support by medically trained personnel). Such a skin treatment device illuminates large skin areas without particularly addressing individual hair follicles. That means that skin tissue without hair follicles is as well irradiated by the treatment light pulse as well as blood vessels being present in the dermal tissue. In order to leave skin tissue and blood vessels thermally unaffected (i.e. to keep the thermal effect on skin tissue and vessels at a level acceptable for home use) in such large area treatment, optimal hair follicle treatment occurs in wavelength ranges in which the melanin absorption is high over the absorption in water and by oxyhemoglobin. Thus, for brownish/blackish hair that carries eumelanin (including blonde hair, i.e. fair brownish hair), the optimal wavelength range is between 630 nm and 900 nm, where the absorption by water and oxyhemoglobin is low in comparison to melanin. Hair removal by light application becomes difficult if eumelanin is essentially missing as chromophore and only pheomelanin can be targeted (i.e. in case of red hair), as the absorption curve for pheomelanin lies below the curve for eumelanin. FIG. 2 show the (mass) extinction coefficient curves for eumelanin and pheomelanin (taken from: T. Sarna, H. M. Swartz, *The physical properties of melanins*, in "The Pigmentary System", ed. J. J. Nordlund et al., Oxford University Press, 1988). The extinction coefficient is a parameter that defines how strongly a substance absorbs light of a certain wavelength. FIG. 2 shows that a treatment light pulse of a certain radiant fluence in the wavelength range of between 630 nm to 900 nm has less an effect on red hair and thus cannot generate a temperature in the hair follicles that is sufficiently high to cause protein coagulation. It is thus believed that red hair is best treated by applying light at a wavelength of around 500 nm (e.g. in a wavelength range of between 480 nm and 510 nm), where oxyhemoglobin has a local absorption minimum (see FIG. 1).

A major factor in setting the right parameters for light based hair removal is the understanding of the absorption of light by the melanin in the skin and the thermal burden on the skin depending on the melanin content of the skin. Melanin content of the skin, i.e. skin color, is generally related to the Fitzpatrick skin type (FST) classification scale, by which FST type I (pale white) to FST type VI (deepest pigmentation) skin types are determined. The more intense the skin color, the higher is the melanin content in the skin and the higher is the light absorption by the melanin particles in the skin and thus the higher is the thermal burden on the skin. Melanin particles in the skin have a typical size in the range of 1 μm to 5 μm, whereas hair follicles have a size in the range of 100 μm to 300 μm. The substantial difference in the size of the melanin carriers (melanin carrying portion of the hair follicles vs. melanin granules in the skin) leads to a different heat dissipation behavior. While the mentioned melanin granules in the skin have a thermal relaxation time of below 0.1 ms, hair follicles have a thermal relaxation time of around 10 ms. Now, it is generally believed that a certain radiant fluence (light energy per unit area) needs to be applied within a certain time frame in order to thermally affect hair follicles. It is believed that the pulse length shall have a value that is above the thermal relaxation time of the melanin granules in the skin in order to allow heat to dissipate from these melanin particles and to reduce the thermal burden on the skin due to light absorption by the pigments. The pulse length may thus in particular be ten times higher than the thermal relaxation time (i.e. at least about 1 ms or above). For pale to medium skin color (FST I-III) the effect of the light absorption of melanin in the skin leads to limited thermal influence and does not play a major role in the determination of optimal pulse length. Anyhow, such short light pulses of 1 ms or even below of a sufficient fluence cannot be generated by today's LED dies even if mounted with a high density as described herein. In accordance with the present disclosure, a pulse length of at least about 10 ms is considered. If the necessary radiant fluence is provided in a too long treatment light pulse, heat dissipation reduces the temperature that can be achieved in a hair follicle to a value too low for effective protein coagulation to occur in the hair follicle. It is believed that the pulse length should not be longer than about 300 ms, in particular not longer than about 200 ms, which value is essentially determined by the thermal relaxation time of the hair follicles, and should typically be in a range of 3 to 10 times the thermal relaxation time (which may be in a range of about 10 ms, but can be higher for large hair follicles). The radiant fluence delivered during this time period shall be in the range of between 1 J/cm$^2$ to 8 J/cm$^2$ in order to achieve an effect relevant for at least temporal hair removal (i.e. a thermally affected change in at least the hair follicle so that a temporal or permanent hair growth reduction occurs). For eumelanin carrying hair and a light skin color, typically 4 J/cm$^2$ to 8 J/cm$^2$ are to be applied. The pulse length may generally be within a range of 10 ms and 300 ms, in particular 20 ms to 200 ms. As mentioned, the skin treatment device may be arranged to emit a treatment light pulse with a pulse length in the range of between 80 ms and 120 ms.

Another factor that is to be taken into account is the penetration depth of the light into the skin. The optical penetration depth (distance where the intensity of the light is reduced to 1/e) seems to vary in literature. E.g. for fair Caucasian skin penetration depth values of 0.230 mm at a wavelength of 500 nm to about 1.6 mm at a wavelength of 1000 nm are provided in one reference (R. Rox Anderson et al., The Optics of Human Skin, The Journal of Investigative Dermatology, 77: 13-19, 1981), while values of about 0.9 mm for 500 nm and 2.6 mm at 1000 nm are provided by another reference (Bashkatov, et. al.; Optical properties of human skin, subcutaneous and mucous tissues in the wavelength range from 400 to 2000 nm; J. Phys. D: Appl. Phys. 38 (2005) 2543-2555). Independent from these differences, the penetration depth generally decreases considerably from a wavelength of 1000 nm to a wavelength of 500 nm. Hair follicles are located at around 1-3 mm below the skin surface. Thus, those wavelengths believed optimal for red hair treatment have a particularly low penetration depth. The low penetration depth of low wavelength light also excludes using light of even lower wavelength, e.g. UV light of around 300 nm, which essentially would not even reach the hair follicles, besides other risks involved with UV light. Because of the strong absorption of light around 500 nm in the skin tissue, it is believed that a radiant fluence in a range of between 3 J/cm$^2$ to about 6 J/cm$^2$, in particular in a range of between 3 J/cm$^2$ to 5 J/cm$^2$, is to be applied.

As has been mentioned before, a light emission unit in accordance with the present disclosure has a substrate on which a plurality of first LED dies each having a certain radiant flux per first LED die is mounted at a sufficiently high density (e.g. between about eight to about 90 LED dies per square centimeter, but the achievable density expressed in number of LED dies per unit area naturally also depends on the size of the LED dies). Some examples of first LED dies suitable in accordance with the disclosure are discussed in the following.

In a first example, a plurality of first LED dies is mounted on a substrate, where each first LED die of the plurality is arranged to emit in a wavelength range of between 680 nm and 780 nm. One example of an LED die emitting in this range is the LED die used in the OSLON SSL® 150 (GF CSHPM1.24—datasheet Version 1.0) from Osram GmbH, Munich, Germany. The respective LED die emits light at a peak emission wavelength of 730 nm (far red) with a spectral bandwidth (FWHM) of $\Delta\lambda=\pm30$ nm. This LED die has a radiant flux (also called radiant power) of between 201 mW and 280 mW (typical 231 mW) at a forward current of 350 mA, where a forward current of up to 1000 mA is specified (leading then to a typical radiant flux of 660 mW).

These LED dies from Osram (having a die size of about 1 mm×1 mm=1 mm$^2$) may be mounted on a substrate with a distance of about 0.2 mm so that 8 times 8=64 LED dies can be mounted on a 1 cm times 1 cm=1 cm$^2$ substrate area.

Generally, large size LED dies may have a size in the range of between 0.5 mm to 1.5 mm times 0.5 mm to 1.5 mm (i.e. a size of 0.25 mm$^2$ to 2.25 mm$^2$). LED dies may be connected to the substrate by wire bonding (in particular gold wire bonding), but in order to achieve a high packaging form factor and enhanced heat dissipation, LED dies may also be connected to the substrate via flip chip technology (a density of 89 1×1 mm$^2$ LED dies per square centimeter may thus be achieved). Driving the above mentioned Osram LED dies (density of 64 LED dies per square centimeter) at the specified forward current of 1000 mA to emit a treatment light pulse having a pulse length of between 30 ms to 200 ms leads to a radiant fluence on the skin (assuming that all radiant energy is applied onto a skin area of the same treatment area size as the mounted substrate area size) in a range of between 1.267 J/cm$^2$ and 8.448 J/cm$^2$. Excess heat generated by the LED dies while emitting light pulses can be dissipated away from the substrate by a passive or active cooling arrangement, e.g. a heat sink, heat pipe, or an active liquid cooling system. Passive cooling arrangements (e.g. heat sinks) may be supported by providing an (cooled) air stream). The efficiency of LED dies often is around 30%, so that a treatment light pulse generating a radiant fluence of 8 J/cm$^2$ means that about 18.7 J/cm$^2$ of excess heat must be dissipated. In contrast to flash lamps that require a certain cooling down time of about 1 s and more, LED dies can be pulsed at a higher frequency and thus a faster overall treatment time of a large skin area can be achieved with LED dies.

In the above described first example, four LED dies from the eight times eight LED die array may be replaced by different LED dies emitting at a second wavelength different to the first wavelength (e.g. the second wavelength could lie in the visible range of between 400 nm and 700 nm) and the fluence on the skin would than still essentially cover a range of between 1 J/cm$^2$ and 8 J/cm$^2$ for a pulse length of between 30 ms and 200 ms.

In a second example, the first LED dies may be taken from the OSLON Black Series (850 nm) from Osram GmbH, Munich, Germany. In accordance with the data sheet (Version 1.1 from 2014-01-09), the respective LED die (size 1×1 mm$^2$) emits light at a peak emission wavelength of 860 nm (centroid wavelength: 850 nm) with a spectral bandwidth (FWHM) of $\Delta\lambda=\pm30$ nm. The total radiant flux is given as 1030 mW at a forward current of 1000 mA. Already five such LED dies mounted on a substrate area of 1 cm$^2$ lead to a radiant fluence of about 1 J/cm$^2$ per 200 ms pulse length on a skin treatment area of 1 cm$^2$ (assuming that the total radiant flux of the LED die is applied onto the skin treatment area).

In a third example, again an array of 8×8 LED dies is mounted on a substrate area of 1 cm$^2$. A first sub-plurality of 44 first LED dies (OSLON SSL® 150 emitting at a first wavelength of 730 nm) is essentially mixed with a second sub-plurality of 20 second LED dies (OSLON Black Series emitting at a second wavelength of 850 nm). If only the first LED dies are switched on to emit a treatment light pulse of 200 ms, a fluence of 5.8 J/cm$^2$ can be achieved. If only the second LED dies (850 nm) are switched on to emit a treatment light pulse of 200 ms, a fluence of above 4 J/cm$^2$ can be achieved. Switched on together, a fluence of almost 10 J/cm$^2$ can be achieved in a 200 ms treatment light pulse (or a fluence of almost 5 J/cm$^2$ in a 100 ms treatment light pulse).

In a further example, Golden DRAGON Plus LV W5AM LED dies from Osram GmbH, Munich, Germany, which emit light at a peak emission wavelength of 502 nm (typical dominant wavelength of 505 nm). In accordance with the datasheet (version 1.1), the LED die has a luminous flux of 67 lm at a forward current of 350 mA. 67 lm convert to a radiant flux of about 240 mW for a wavelength of 505 nm (about 684 mW at 1000 mA forward current when a linear extrapolation is used). As the 505 nm dominant wavelength LED die emits in a spectral band around the dominant wavelength and as the lumen to Watt conversion is strongly depending on the wavelength, this value is just an estimate. Around twenty-one such 505 nm LED dies are needed per square centimeter to achieve a radiant fluence of about 3 J/cm$^2$ in a 200 ms treatment light pulse. Hence, about forty-four 505 nm LED dies per square centimeter provide the radiant fluence of 3 J/cm$^2$ in a 100 ms pulse and about eighty-eight 505 nm LEDs provide a radiant fluence about 6 J/cm$^2$ in a 100 ms pulse. About eighty-eight 505 nm LED dies can provide a radiant fluence of about 3 J/cm$^2$ in a 50 ms pulse. The hair removal device may additionally comprise a plurality of such LED dies in order to additionally provide red hair treatment capability. The at least one second LED die may be a Golden DRAGON Plus LV W5AM LED die. While these LED dies can be used as first LED dies for emitting treatment light, they can also be used as second LED dies for visibly indicating the selected active area of first LED dies. Hence, in some embodiments, first and second LED dies are of the same type (e.g. of the type described in this paragraph) and the second LED dies are used outside of the treatment pulse duration for the visible indication of the selected active area and are used together with the first LED dies during the treatment pulse duration for the emission of treatment light.

It is to be understood that the values discussed here are relatively rough reference values, as the radiant flux of an LED die depends on the temperature of the LED die, the forward current and other factors.

Table 1 is a summary of wavelength, pulse length and fluence values that the inventors of the present description believe to represent optimal treatment parameters for the given hair color and FST skin type. The wavelength is understood to be a representation of a wavelength range in each case, which range should cover a range of ±50 nm (optionally ±30 nm) around the given single wavelength value. It is noted that in some embodiments the skin treatment device comprises a first sub-plurality of first LED dies arranged for emitting light with a peak emission wavelength around 730 nm and a second sub-plurality of first LED dies arranged for emitting light with a peak emission wavelength around 850 nm so that a control unit can activate the first LED dies in accordance with Table 1 (excluding the red hair situations). Additionally, a third sub-plurality of first LED dies arranged for emitting light with a peak emission wavelength around 500 nm may be present, so that the control unit can activate the first LED dies in accordance with Table 1.

TABLE 1

Wavelength, fluence and pulse length values provided as a function of hair color and FST skin type. It is to be understood that the wavelength shall represent a range of wavelengths of ±50 nm around the given single wavelength value.

| Hair color | Skin Type [FST] | Wavelength [nm] | Pulse length [ms] | Fluence [J/cm$^2$] |
|---|---|---|---|---|
| Light brown/medium | I-II | 730 | 20-200 | 4-7 |
| Dark brown | I-II | 730 | 20-200 | 2-5 |
| Red | I-II | 500 | 30-200 | 3-5 |
| Light brown/medium | III-IV | 730 + 850 | 20-200 | 4-7 |
| Dark brown | III-IV | 730 + 850 | 20-200 | 2-5 |
| Red | III-IV | 500 | 100-200 | 3-5 |
| Light brown/medium | V-VI | 850 | 30-200 | 4-7 |
| Dark brown | V-VI | 850 | 30-200 | 2-5 |
| Red | V-VI | — | — | — |
| White/grey | All | — | — | — |

Figure 3:
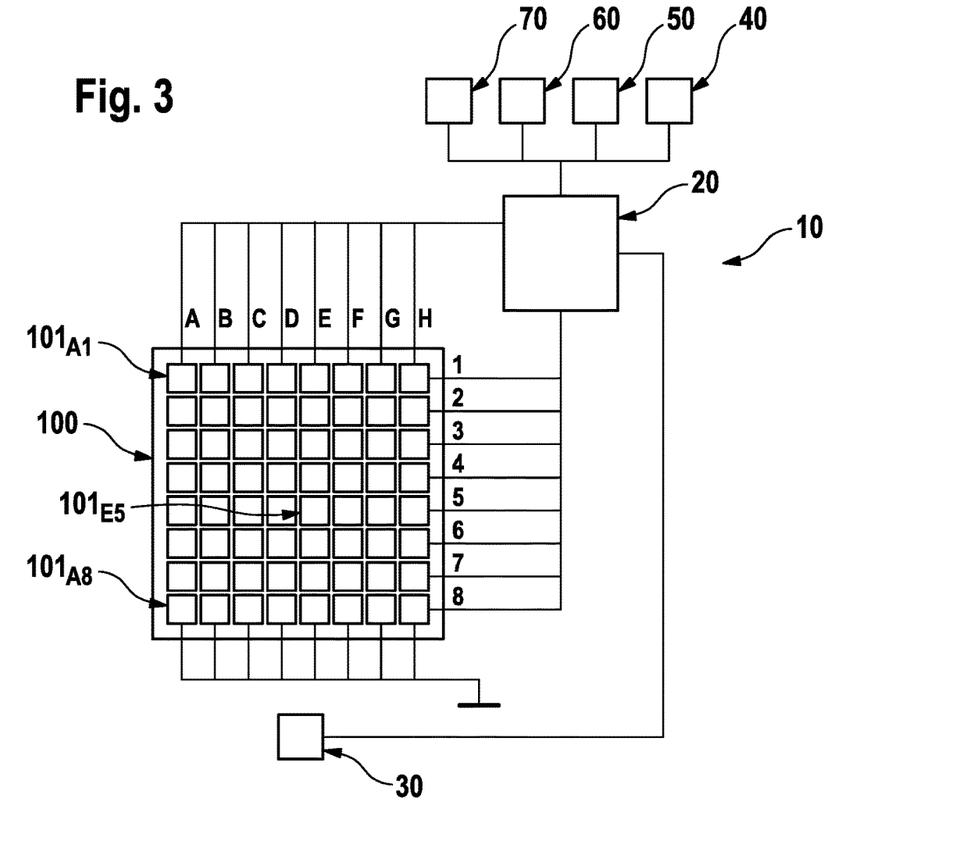
FIG. 3 is a schematic depiction of an example embodiment of a light emission unit in accordance with the present disclosure, which comprises a substrate on which an eight times eight matrix of LED dies is mounted.

FIG. 3 is a schematic depiction of an example embodiment of a light emission unit 10 in accordance with the invention. The light emission unit 10 comprises a substrate 100 on which a plurality of 64 LED dies are mounted. The LED dies are arranged in a regular rectangular 8 times 8 pattern in columns A to H and rows 1 to 8, so that the LED dies can be identified by their position in the column-row matrix. Three LED dies $101_{A1}$, $101_{A8}$, and $101_{E5}$ are exemplary identified and it shall be understood that LED dies in a matrix arrangement can be identified by their column and row added as a suffix to the respective reference numeral.

Figure 4A:
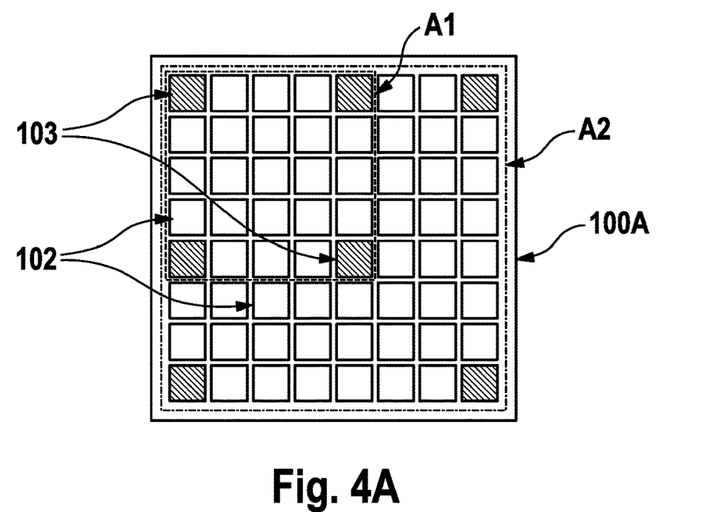
FIG. 4A is another example embodiment of an eight times eight matrix of LED dies mounted on a substrate comprising first and second LED dies.
Figure 4B:
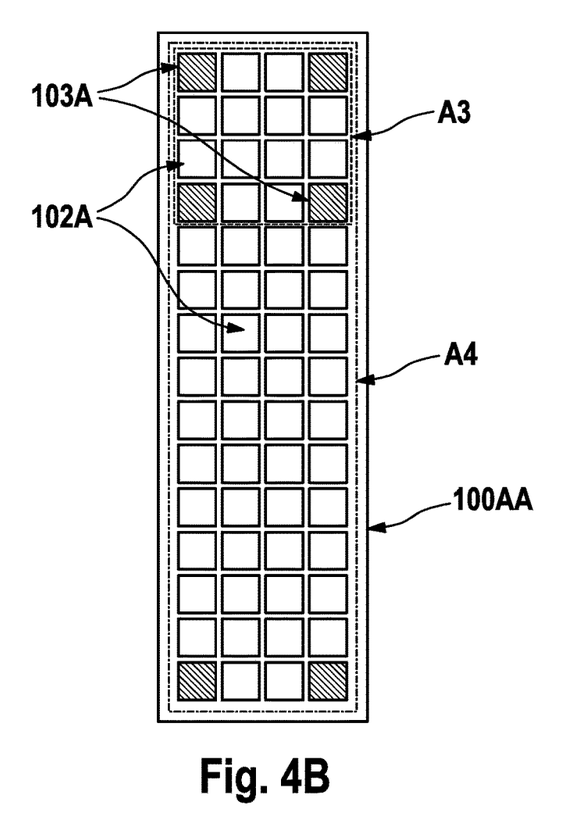
FIG. 4B is an example embodiment of a fifteen times four matrix of LED dies mounted on a substrate comprising first and second LED dies.
Figure 5:
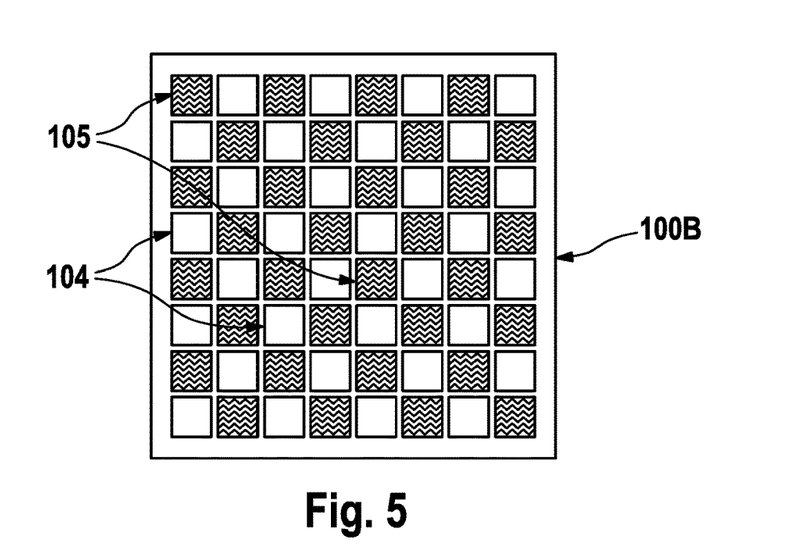
FIG. 5 is another example embodiment of an eight times eight matrix of LED dies mounted on a substrate comprising first and second LED dies.
Figure 6:
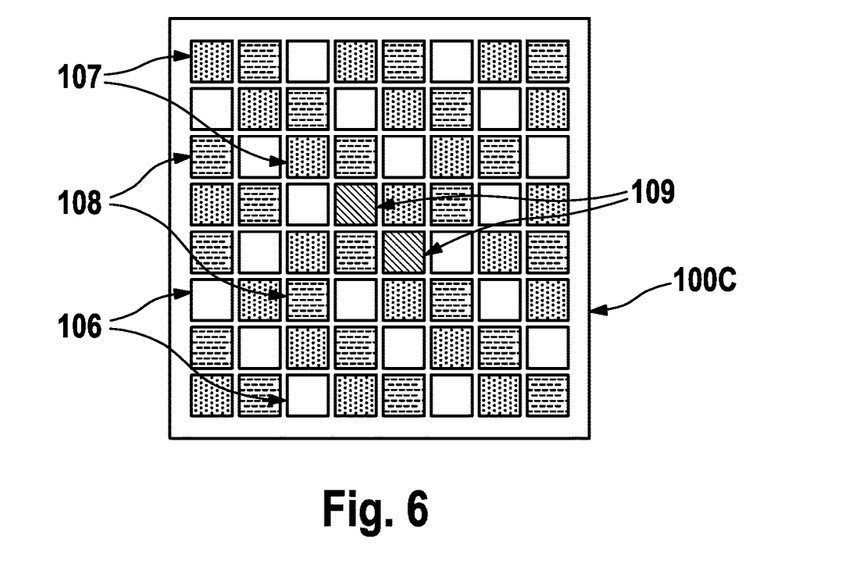
FIG. 6 is a further example embodiment of an eight times eight matrix of LED dies mounted on a substrate comprising different sub-pluralities of first LED dies.

It is to be understood that the shown 8 times 8 square LED die matrix is just an example and the LED dies may be arranged on the substrate in any sensible manner, either as a regular square or rectangular matrix such as a 2 times 2, a 2 times 4, a 3 times 6, a 5 times 5, a 10 times 14, a 4 times 15 (see FIG. 4B) etc. matrix or in a less structured, more random pattern. Instead of being arranged in a regular square or rectangular matrix, the LED dies may be arranged in a regular pattern, which resembles a circular region rather than a square or rectangular region. Any other shape of the mounted substrate area may be chosen as well (e.g. triangular, trapezoidal, arbitrary). In the examples of FIGS. 4A, 5 and 6, the same 8 times 8 matrix will be used for sake of simplification of the discussion, but the concepts and ideas described with respect to these figures are of course also applicable to the just mentioned other regular or irregular patterns of substrate mounted LED dies. FIG. 4B shows an embodiment with a 4 times 15 matrix.

A control unit 20 has leads connected with the matrix of LED dies in order to selectively provide voltage and current supply to each of the LED dies 101. As mentioned before, the 8 times 8 matrix has 8 columns of LED dies that are connected in series so that each of the columns is controlled at the same instant. Generally, while the control unit 20 may be arranged to simultaneously switch on and off all LED dies, the control unit 20 may also be arranged to individually switch on or off each of the LED dies mounted on the substrate. Generally, a control unit may be connected with the plurality LED dies in any suitable manner.

Control unit 20 is coupled with a sensor 30 for measuring a skin property, e.g. the skin color (pigmentation level). The sensor may comprise a light source that is illuminating the skin and the sensor may be arranged to determine the skin property such as skin color from the amount of light that is backscattered to the sensor (e.g. realized by a photo diode).

The control unit 20 may then in particular be arranged to control at least one treatment parameter based on the measured skin color, e.g. light intensity and/or pulse length. The sensor 30 is to be understood as an optional feature.

The control unit 20 is here also coupled with a user interface 40, 50, 60, 70 allowing the user to control aspects of the light emission unit 10. The user interface here comprises four input elements 40, 50, 60, and 70. A first input element 40 may be arranged as an ON/OFF switch. A second input element 50 may be arranged as a switch to choose a treatment type, e.g. the second input element 50 may allow a user to switch between a hair removal function and a skin rejuvenation function. The control unit 20 may then be arranged to control at least one treatment parameter based on the chosen type of treatment, e.g. the radiant flux emitted by the LED dies may be lower for a skin rejuvenation function than for a hair removal function. A third input element 60 may be arranged to allow the user to input the hair color. The control unit 20 may then be arranged to control at least one treatment parameter in dependence on the hair color. A fourth input element 70 may be arranged to allow the user to set a maximum radiant fluence value to be applied onto the skin (e.g. a value in the range of between 1 J/cm$^2$ and 8 J/cm$^2$). The control unit 20 may then be arranged to apply only light pulses with a radiant fluence not higher than the chosen maximum radiant fluence. Additionally or alternatively, one of the input elements may be arranged to allow the user to switch from a first active area of the mounted first LED dies to second active area (see description with reference to FIGS. 4A and 4B below). Each of the input elements 40, 50, 60, or 70 may be arranged as an input knob or a slider or as a touch sensitive switch on a touch sensitive board. In contrast of being wire-connected with the control unit 20, the user interface may be realized on a separate device that is connected with the control unit 20 in a wireless manner. Instead of four input elements as shown in FIG. 3, the user interface may have one, two, three, five, six or any number of input elements. In some embodiments, the light emission unit 10 is free of any user interface and may be arranged to operate in an automated manner. Other or additional functions than the functions as described above may be realized via the user interface.

FIG. 4A shows one example arrangement of a plurality of first and second LED dies 102 and 103 mounted on a substrate 100A. A plurality of first LED dies 102 has 57 members. A plurality of second LED dies 103 has seven members. The seven members of the plurality of second LED dies 103 are identified by their matrix positions as $103_{A1}$, $103_{E1}$, $103_{H1}$, $103_{A5}$, $103_{E5}$, $103_{A8}$, and $103_{H8}$. The plurality of first LED dies 102 may be arranged to emit at a far red or infrared (IR) wavelength (first wavelength), which is essentially invisible to the human eye. The first LED dies may be used for applying a treatment light pulse to a skin surface. The second LED dies 103 may be arranged to emit in the visible wavelength range of between 400 nm and 700 nm (second wavelength different to first wavelength), and the second LED dies may in particular be arranged as low radiant flux LED dies not suitable for emitting light at an intensity level sufficient for temporal hair removal (e.g. the second LED dies may have a specified forward current of below 100 mA, in particular of around 50 mA or 20 mA at around 2 V supply voltage). The second LED dies are used to indicate a selected active area of the first LED dies in a time period outside of the duration of the treatment light pulse. Switched on second LED dies $103_{A1}$, $103_{E1}$, $103_{A5}$, and $103_{E5}$ then indicate that only the first LED dies arranged between those four second LED dies will be used for applying treatment light to the skin (the first selectable active area A1 is indicated by a dashed line), while switched on second LED dies $103_{A1}$, $103_{H1}$, $103_{A8}$, and $103_{H8}$ indicate that the full plurality of first LED dies will be used (the second selectable active area A2 is indicated by a dashed-dotted line). The smaller first selectable active area A1 may be useful for facial skin treatment (the smaller selectable active area A1 allows more precisely targeting small facial regions), while the larger selectable active area A2 may be useful for body skin treatment (faster treatment). As already mentioned above, an input element may be provided to allow a user to select one of the selectable active areas. In this example, the first LED dies lying within the first selectable active area A1 are assigned to the first selectable active area and the first LED dies lying within the second selectable active area A2 (which means all of the plurality of first LED dies) are assigned to the second selectable active area A2. The second LED dies $103_{A1}$, $103_{E1}$, $103_{A5}$, and $103_{E5}$ are assigned to the first selectable active area A1 and the second LED dies $103_{A1}$, $103_{H1}$, $103_{A8}$, and $103_{H8}$ are assigned to the second selectable active area A2. The second LED dies are here arranged in the corners of the rectangular selectable active areas. The second LED die $103_{A1}$ is assigned to both selectable active area as it is arranged in a common corner of the selectable active areas.

Depending on the pattern of the LED dies, at least two second LED dies may be used to indicate the selected active area (e.g. the second LED dies may be arranged in the opposite corners of a square or rectangular arrangement). In some embodiments, the active area of first LED dies may be surrounded by second LED dies to indicate the active area. Instead of an arrangement as shown in FIG. 4A, the second LED dies located in the corners may be replaced by first LED dies and the respective second LED dies may then be arranged outside of the shown 8 time 8 matrix, in close proximity to the corner points. E.g. by way of expanding the matrix, the second LED dies for indicating the second (larger) selectable active area A2 may then be located at locations (A,0), (A,9), (H,0), and (H,9).

As was mentioned before and by way of a general explanation, the second LED dies are used to visibly indicate the selected active area outside of the duration of the treatment pulse. E.g. a user may switch on the skin treatment device. Then either no second LED die is activated (and the device awaits a selection) or the active area is indicated that was selected prior to switching off the device or one of the selectable active areas is used as a standard selection and the respective second LED dies assigned to this standard selectable active area are activated to visibly indicate the selected active area. A control element may be present to allow the user to switch on and off the visible indication of the selected active area.

Generally, in some embodiments, just one of the at least three second LED dies is used to generate a visible light pulse simultaneously with the treatment light pulse. The second LED die may in particular be arranged to emit light at a low radiant flux (e.g. below 100 mW, typically with a forward current of around 20 mA to 50 mA). The second LED die is controlled to emit the visible light pulse simultaneously with the emission of the treatment light pulse, which may be invisible to the human eye because it lies, e.g. in the far red or IR wavelength range above 700 nm.

FIG. 4B shows an example embodiment of an four times fifteen LED die matrix mounted on a substrate 100AA similar to the embodiment shown in FIG. 4A, where in addition to a plurality of 54 first LED dies 102A arranged for emitting treatment light pulses a plurality of six second LED dies 103A is arranged to emit light in the visible wavelength range in order to indicate a first selectable active area A3 or a larger second selectable active area A4. Such a rectangular LED die array may in particular be used in a skin treatment device that is continuously moved over the skin instead of subsequently moved from one skin treatment area to another skin treatment area, for which an LED die array as shown in FIG. 4A may be used. The gliding movement may occur in particular in a direction perpendicular to the long axis of the rectangular LED die array. In some embodiments, a glidingly utilized skin treatment device may comprise a speed sensor for determining the speed by which the device is moved across the skin. The skin treatment device may then be arranged to control the time period between consecutive treatment light pulses in dependence on the determined gliding speed, so that the treatment light pulses are seamlessly applied onto the skin (i.e. essentially without gaps or overlap). Due to the rectangular shape, the smaller active area A3 covers the full width of the LED matrix, which helps in a precise positioning of the small active area A3 onto the treatment area.

FIG. 5 shows an example embodiment of an 8 times 8 matrix of LED dies, where a first sub-plurality of thirty-two first LED dies 104 and a second sub-plurality of thirty-two first LED dies 105 are mounted on a substrate 100B in a checkerboard pattern (e.g. leading to an essentially homogeneous distribution of the LED dies over the mounted substrate area). In particular in cases where the array of mounted LED dies is located close to the skin to be treated during operation, an essentially homogeneous illumination can be achieved by either activating only the first sub-plurality of first LED dies or the second sub-plurality of first dies. The first sub-plurality of first LED dies 104 may be arranged to emit light at a first wavelength (in particular at an intensity level sufficient for at least temporal hair removal) and the second sub-plurality of first LED dies may be arranged to emit at a second wavelength different to the first wavelength. The second sub-plurality of first LED dies may emit at a radiant flux that is alone also sufficient for at least temporal hair removal, but the second LED dies may also emit at a radiant flux that is sufficient for skin rejuvenation or other skin treatments. While not shown in this embodiment, it shall be understood that the second LED dies are located in close proximity to the corners of the selectable active areas as was explained with reference to FIG. 4A. Instead of being arranged in a checkerboard pattern, the first and second sub-pluralities of first LED dies may also be arranged in any other pattern and there may be more or less first LED dies of the first sub-plurality than first LED dies of the second sub-plurality (e.g. two, seven, ten, sixteen, twenty, forty etc.). As had been mentioned before, the here depicted eight times eight matrix is just for illustration purposes and any arbitrary number of first LED dies may be arranged in any arbitrary pattern, as long as at least the first LED dies are arranged to generate a radiant fluence of at least 1 J/cm$^2$ on the skin during regular operation in a pulse having a pulse length of between 10 ms to 300 ms, i.e. the first LED dies emit light with at least 3.333 W/cm$^2$ (assuming that the area of the active array of first LED dies is emitting onto a skin area of the same size).

FIG. 6 shows another example embodiment of an 8 times 8 matrix of LED dies mounted on a substrate 100C, where four different sub-pluralities of first LED dies are mounted on the substrate 100C. A first sub-plurality of twenty first LED dies 106, a second sub-plurality of twenty-one first LED dies 107, and a third plurality of twenty-one first LED dies 108 are mounted on the substrate in an alternating fashion. In the center of the LED die array a fourth sub-plurality of two first LED dies 109 is mounted that may be arranged to emit in a visible wavelength range at a radiant flux suitable for illumination purposes (i.e. for emission of a visible light pulse simultaneously with the emission of the treatment light pulse). In some embodiments, the first sub-plurality of first LED dies 106 may be arranged to emit at a first wavelength (e.g. at 850 nm), the second sub-plurality of first LED dies 107 may be arranged to emit at a second wavelength different to the first wavelength (e.g. 730 nm) and the third plurality of first LED dies 108 may be arranged to emit at a third wavelength (e.g. 505 nm) different to the first and second wavelength.

Figure 7A:
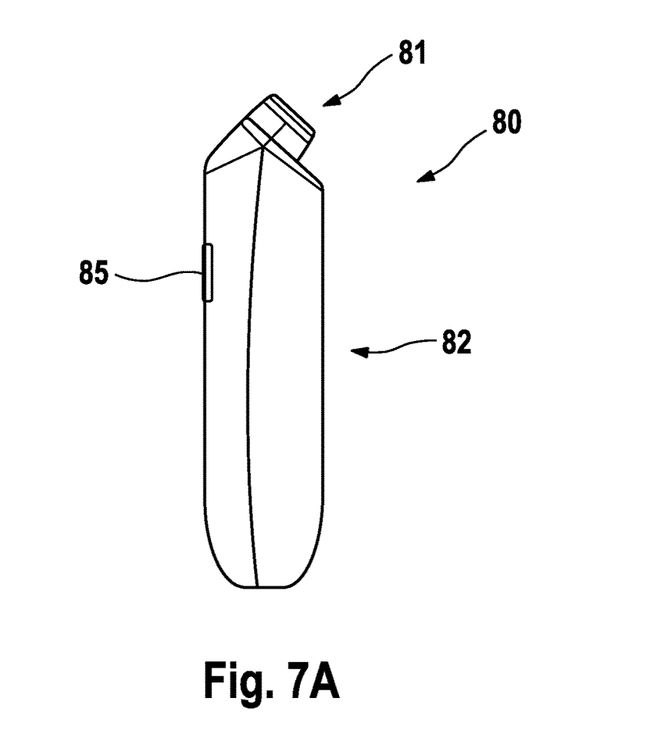
FIG. 7A is a side view of an example embodiment of a skin treatment device in accordance with the present disclosure.
Figures 7B, 7C:
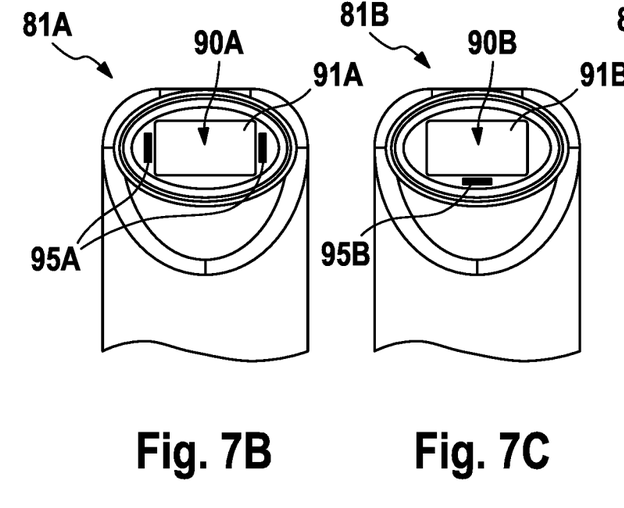
FIGS. 7B-D are front views onto various example head sections of a skin treatment device as shown in FIG. 7A, where different positions of one or more additional sensors for measuring a skin property is indicated.
Figure 7D:
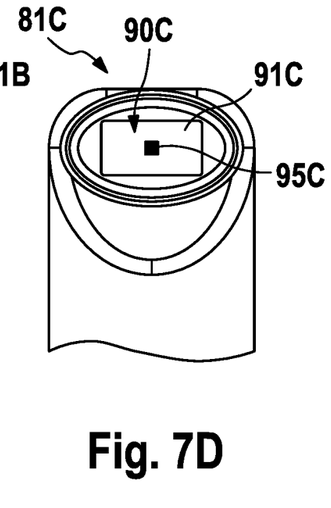

FIG. 7A shows a depiction of a skin treatment device 80 in accordance with the present invention. A light emission unit as described in the previous paragraphs is used in the skin treatment device 80. The skin treatment device 80 has a head section 81 for emission of treatment light pulses and a handle section 82 for holding of the skin treatment device 80 by a user's hand. A control element 85 is arranged at the handle section 82 for at least switching ON/OFF the skin treatment device 80. FIGS. 7B to 7D show front views of different embodiments of the head section 81A, 81B, 81C, where the embodiments differ essentially only in the location of a sensor or several sensors 95A, 95B, 95C for measuring at least one skin property. The head sections 81A, 81B, 81C each have a respective exit opening 90A, 90B, or 90C through which the treatment light pulses will be emitted during operation. A substrate with a plurality of LED dies mounted on the substrate may be arranged closely behind the exit opening 90A, 90B, 90C or the substrate may be arranged with a certain distance of about or less than 10 mm to the exit opening 90A, 90B, 90C inside of the head section 81A, 81B, 81C. An exit window 91A, 91B, 91C made from a material being essentially transparent to the light to be emitted by the LED dies covers the exit opening 90A, 90B, 90C. The exit opening 90A, 90B, 90C may have a size in the range of between 0.2 $cm^2$ to 10 $cm^2$, in particular in the range of 1 $cm^2$ to 4 $cm^2$. The mounted area of the substrate may then have the same size and shape as the exit opening 90A, 90B, 90C. In some embodiments, no exit window 91A, 91B, 91C is present. In the embodiment of FIG. 7B, the skin treatment device comprises two sensors 95A for measuring at least one skin property, which two sensors 95A are arranged on two opposite sides of the exit opening 90A. In the embodiments shown in FIGS. 7C and 7D, only a single sensor 95B and 95C, respectively, for measuring at least one skin property is arranged on the head section 81B and 81C, respectively. In FIG. 7C, the sensor 95B is arranged underneath the exit opening 90B, so that the sensor 95B is arranged before the exit opening 90B with respect to the usual movement direction (the device in accordance with FIG. 7C may be used in gliding mode). In FIG. 7D, the sensor 95C is arranged in a center area of the exit opening 90C. In such a case, the substrate disposed close to the exit opening 90C may have a respective cutout so that the sensor can be arranged in the cutout or can operate through the cutout. The sensor or sensors 95A, 95B, 95C may also allow determining skin contact, so that a control unit of the light emission unit may be arranged to only trigger the emission of a treatment light pulse in case a skin contact is determined.

Figure 8:
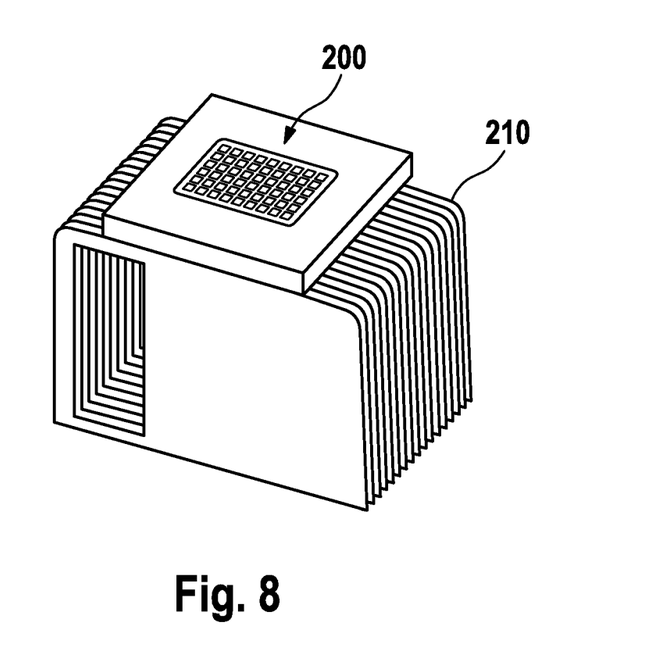
FIG. 8 is a schematic depiction of an array of LED dies mounted on a substrate, which substrate is in turn mounted on a heat sink to carry away excess heat.

FIG. 8 is a depiction of a substrate mounted LED die array 200 that is mounted on a heat sink 210 to convey away excess heat generated by the LED dies in operation. A fan may be arranged close to the heat sink to support the heat dissipation away from the heat sink.

Figure 9A:
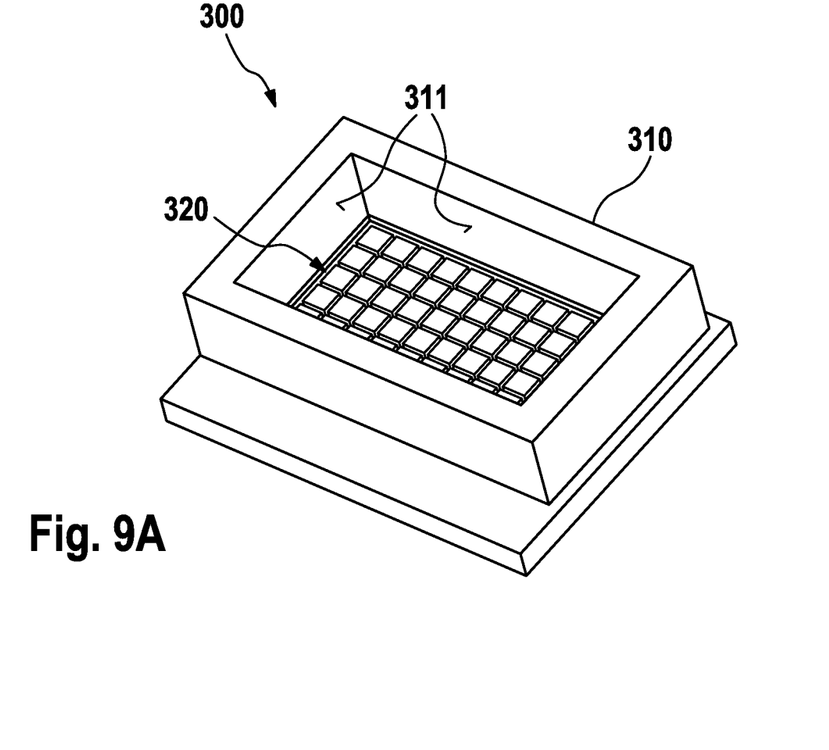
FIG. 9A is a depiction of an array of LED dies mounted on a substrate with a casing having inner reflective walls arranged around the mounted substrate area.
Figure 9B:
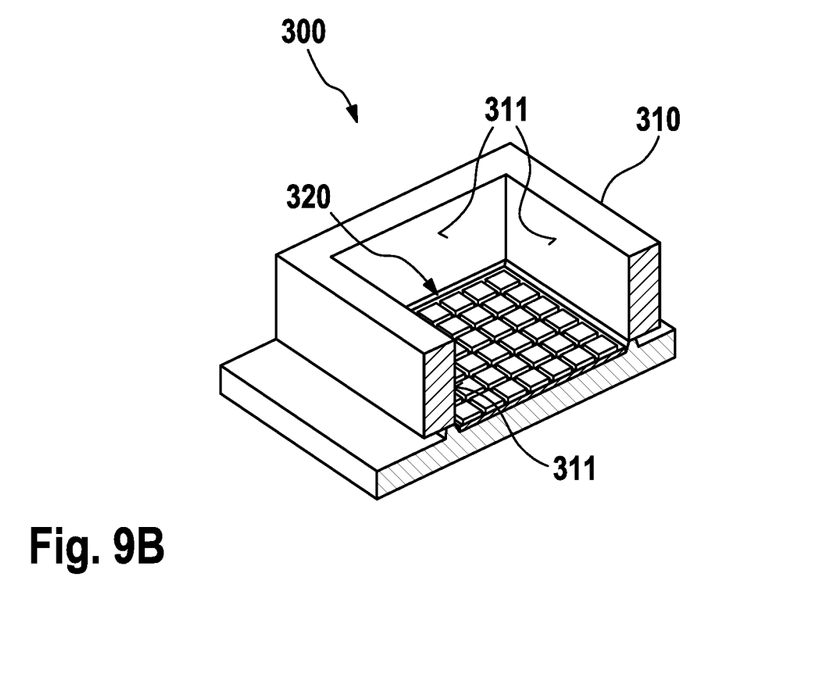
FIG. 9B is a cut-open depiction of the LED array with casing shown in FIG. 9A.

FIGS. 9A and 9B show a perspective view and a cut through a substrate mounted LED die array 300, where a casing 310 is mounted around the mounted area 320. The casing 310 has inner wall surfaces 311 that are highly reflective for the light that is emitted by the first LED dies. The inner wall surfaces 311 may have a reflective coating, may be made from polished metal or from a diffusely reflecting plastic or ceramic material. The casing 310 then serves to guide the light emitted by the first LED dies in an essentially loss-free manner from the first LED die level to an exit opening of the skin treatment device and the radiant flux on the level of the first LED dies is essentially the same as the radiant flux measured on the treatment area when the exit opening is placed on the skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin treatment device, in particular a hair removal device, comprising
    a light emission unit comprising a substrate and a plurality of first LED dies mounted on the substrate on an area in the range of between about 0.2 $cm^2$ and about 100 $cm^2$,
    wherein the skin treatment device is arranged to activate the first LED dies to emit a treatment light pulse having a pulse length and the first LED dies have a radiant flux such that a radiant fluence on the skin of a user in a range between about 1 $J/cm^2$ and about 30 $J/cm^2$ is achieved by application of the treatment light pulse,
    wherein the light emission unit has at least two selectable active areas of first LED dies, where the selectable active areas have different sizes, and at least three second LED dies are mounted on the substrate at locations suitable for visibly indicating each of the selectable active areas.

2. The skin treatment device in accordance with claim 1, wherein the first LED dies are mounted on the substrate on an area in the range of between 1.0 $cm^2$ and about 10 $cm^2$.

3. The skin treatment device in accordance with claim 1, wherein the pulse length is in a range of between about 10 ms and about 300 ms.

4. The skin treatment device in accordance with claim 1, wherein the second LED dies are disposed at corners or end points of the selectable active areas of first LED dies or are mounted in close proximity to such corners or end points of the selectable active areas of first LED dies.

5. The skin treatment device in accordance with claim 1, further comprising a control unit for controlling the first and second LED dies.

6. The skin treatment device in accordance with claim 5, wherein the control unit is arranged for activating only the first LED dies assigned to the selected active area to emit the treatment light pulse and for activating only the second LED dies assigned to the selected active area to emit visible light outside of the duration of the treatment light pulse to visibly indicate the selected active area.

7. The skin treatment device in accordance with claim 1, wherein the at least three second LED dies are each arranged for emitting light with a peak emission wavelength in the visible wavelength range of between about 400 nm and about 700 nm at a radiant flux lower than the radiant flux required for achieving at least temporal hair removal.

8. The skin treatment device in accordance with claim 7, wherein the radiant flux of the second LED dies is in a range of between about 0.1 mW and about 100 mW.

9. The skin treatment device in accordance with claim 1, wherein at least six second LED dies are mounted on the substrate.

10. The skin treatment device in accordance with claim 1, further comprising a user-operable control element for selecting one of the selectable active areas.

11. The skin treatment device in accordance with claim 1, wherein the skin treatment device is arranged to control the second LED dies for emitting a visible light pulse simultaneously with the emission of the treatment light pulse.

12. The skin treatment device in accordance with claim 11, wherein the first LED dies are arranged to emit at a peak emission wavelength in the far red to infrared wavelength range of between about 700 nm and about 980 nm.

13. The skin treatment device in accordance with claim 1, wherein the mounted substrate area is surrounded by a casing defining an inner chamber of essentially the shape and area of the mounted substrate area, the casing having inner walls that are reflective with respect to at least the light emitted by the first LED dies so that the radiant flux of the first LED dies per unit area is essentially preserved until an exit opening of the casing.

14. The skin treatment device in accordance with claim 1, wherein the size of the smaller of the selectable active areas lies in the range of between about 0.10 cm$^2$ and about 2.0 cm$^2$.

15. The skin treatment device in accordance with claim 1, further comprising an exit opening, wherein each of said the first LED dies and the area of the exit opening is separated by a vertical distance in a range of between about 0.1 mm and about 10 mm.

16. The skin treatment device in accordance with claim 1, further comprising a control element for switching between a first skin treatment function and a second skin treatment function.

17. A method of skin treatment comprising the steps of:
providing a substrate;
mounting a plurality of first LED dies onto the substrate on an area in the range of between about 0.2 cm$^2$ and about 100 cm$^2$, which first LED dies are arranged for emitting light with a peak emission wavelength in the wavelength range of between about 480 nm and about 980 nm;
mounting at least three second LED dies onto the substrate at locations suitable for visibly indicating each one of at least two selectable active areas of the plurality of first LED dies;
selecting an active area from the at least two selectable active areas;
activating the first LED dies assigned to the selected active area to emit a treatment light pulse; and
activating at least two of the at least three second LED dies to emit visible light to indicate the selected active area for duration of the treatment light pulse.

18. The method in accordance with claim 17, further comprising the step of:
controlling the second LED dies to emit visible light at a radiant flux in the range of between about 0.1 mW and about 100 mW per second LED die[s].

19. The method in accordance with claim 17, further comprising the steps of:
selecting the first LED dies to emit light with a peak emission wavelength in the far red to infrared wavelength range of between about 700 nm and about 980 nm; and
controlling at least one of the second LED dies to emit a visible light pulse simultaneously with the treatment light pulse.

* * * * *